(12) United States Patent
Bogle

(10) Patent No.: US 11,272,968 B2
(45) Date of Patent: Mar. 15, 2022

(54) SLOTTED PERIPROSTHETIC PLATE FOR VARIABLE ANGLE HOLES

(71) Applicant: DePuy Synthes Products, Inc., Raynham, MA (US)

(72) Inventor: David W. Bogle, Coatsville, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 191 days.

(21) Appl. No.: 16/150,747

(22) Filed: Oct. 3, 2018

(65) Prior Publication Data
US 2020/0107867 A1 Apr. 9, 2020

(51) Int. Cl.
*A61B 17/80* (2006.01)
*A61B 17/74* (2006.01)
*A61B 17/72* (2006.01)

(52) U.S. Cl.
CPC ........ *A61B 17/8061* (2013.01); *A61B 17/744* (2013.01); *A61B 17/746* (2013.01); *A61B 17/8014* (2013.01); *A61B 17/8033* (2013.01); *A61B 17/8052* (2013.01); *A61B 17/7233* (2013.01)

(58) Field of Classification Search
CPC ... A61B 17/744; A61B 17/746; A61B 17/748; A61B 17/742; A61B 17/74; A61B 17/7241; A61B 17/725; A61B 17/7233; A61B 17/8047; A61B 17/8033; A61B 17/8009; A61B 17/8014; A61B 17/8004; A61B 17/8061
See application file for complete search history.

(56) References Cited

U.S. PATENT DOCUMENTS

| | | | |
|---|---|---|---|
| 1,025,008 A | * | 4/1912 | Miner ............... A61B 17/7059 606/71 |
| 3,604,414 A | | 9/1971 | Borges |
| 3,659,595 A | | 5/1972 | Haboush |
| 5,041,113 A | | 8/1991 | Biedermann et al. |
| 5,234,431 A | | 8/1993 | Keller |
| 5,344,421 A | | 9/1994 | Crook |
| 5,486,176 A | | 1/1996 | Hildebrand et al. |
| 5,522,902 A | | 6/1996 | Yuan et al. |

(Continued)

FOREIGN PATENT DOCUMENTS

| | | |
|---|---|---|
| WO | 2010117940 A1 | 10/2010 |
| WO | 2010124205 A1 | 10/2010 |

*Primary Examiner* — Amy R Sipp
(74) *Attorney, Agent, or Firm* — Kramer & Amado, P.C.

(57) ABSTRACT

A bone plate comprises a body including an elongated opening extending therethrough, the opening being open at a distal end of the body and including a distal portion and a proximal portion, the distal portion having a width smaller than a width of the proximal portion, the width being a dimension between two longitudinal sides of the opening extending parallel to a longitudinal axis of the body, the body further including an insert including a head portion and a base portion, the base portion being shaped to be slidably mounted within the proximal portion of the opening, a diameter of the base portion being larger than a width of the distal portion of the opening such that the base portion is prevented from exiting the opening through the distal portion thereof, the insert further including a central fixation element receiving hole configured to receive a bone fixation element therethrough.

15 Claims, 4 Drawing Sheets

(56) References Cited

U.S. PATENT DOCUMENTS

| | | | |
|---|---|---|---|
| 5,951,557 A * | 9/1999 | Luter | A61B 17/80 606/286 |
| 8,753,343 B2 | 6/2014 | Staeubli | |
| 2002/0111630 A1* | 8/2002 | Ralph | A61B 17/8023 606/71 |
| 2005/0010218 A1* | 1/2005 | Dalton | A61B 17/7059 606/304 |
| 2006/0100623 A1 | 5/2006 | Pennig | |
| 2008/0097445 A1* | 4/2008 | Weinstein | A61B 17/8023 606/281 |
| 2008/0140077 A1* | 6/2008 | Kebaish | A61B 17/863 606/64 |
| 2008/0249572 A1 | 10/2008 | Tandon | |
| 2010/0256685 A1 | 10/2010 | Plecko et al. | |
| 2010/0262194 A1 | 10/2010 | Wagner et al. | |
| 2010/0298829 A1 | 11/2010 | Schaller et al. | |
| 2014/0094856 A1* | 4/2014 | Sinha | A61B 17/7059 606/291 |
| 2014/0121710 A1* | 5/2014 | Weaver | A61B 17/8625 606/286 |
| 2016/0206356 A1 | 7/2016 | Koay et al. | |

* cited by examiner

SLOTTED PERIPROSTHETIC PLATE FOR VARIABLE ANGLE HOLES

FIELD OF INVENTION

The invention relates to a bone plate to be used for the treatment of fractured bones.

BACKGROUND

Distal femoral fractures and periprosthetic fractures around implants are often treated using a combination of an intramedullary nail and a bone plate. Locking holes in the nail generally dictate the location at which a bone plate could be mounted. Therefore, the plate location is often determined by the surgeon's placement of the intramedullary nail (e.g., the amount the surgeon recesses and rotates the nail). Due to the specific bone geometry and varying bone anatomy from one patient to another, the adjustment of the plate location to fit each patient can be difficult. This case-by-case adjustment of the plate may increase operation room time potentially increases the cost of the fracture treatment system as multiple designs are often needed to accommodate varying intramedullary nail and plate placements.

SUMMARY

The present embodiments are directed to a bone plate for treating periprosthetic fractures, comprising a body extending from a proximal end to a distal end and including an elongated opening extending therethrough from a first surface of the body which, when the bone plate is in an operative position, faces away from the bone, to a second surface which, when the bone plate is in an operative position, faces toward the bone, the opening being open at the distal end of the body and including a distal portion and a proximal portion, the distal portion having a width that is smaller than a width of the proximal portion, the width being a dimension between two longitudinal sides of the opening extending parallel to a longitudinal axis of the body, the body further including at least one bone fixation element receiving opening extending therethrough from the first surface to the second surface and an insert including a head portion and a base portion, the base portion being sized and shaped to be slidably mounted within the proximal portion of the opening, a diameter of the base portion being larger than a width of the distal portion of the opening such that the base portion, when positioned within the proximal portion of the opening, is prevented from exiting the opening through the distal portion thereof, the insert further including a central fixation element receiving hole configured to receive a bone fixation element therethrough.

The present embodiments are also directed to a bone plate for treating periprosthetic fractures comprising a body extending from a proximal end to a distal end and including an elongated opening extending therethrough from a first surface of the body which, when the bone plate is in an operative position, faces away from the bone, to a second surface which, when the bone plate is in an operative position, faces toward the bone, the opening being open at the distal end of the body, the opening including two sliding ledges formed within inner longitudinal surfaces thereof, the sliding ledges extending from a proximal to the distal end of the body and an insert including a head portion and a base portion, the head portion being sized and shaped to be slidably mounted within the sliding ledges of the body, the insert further including a central fixation element receiving hole configured to receive a bone fixation element therethrough.

The present embodiments are also directed to a system for treating periprosthetic fractures comprising an intramedullary nail including a through hole configured to receive a bone fixation element, a bone plate extending from a proximal end to a distal end and including an elongated opening extending therethrough from a first surface of the bone plate which, when the bone plate is in an operative position, faces away from the bone, to a second surface which, when the bone plate is in an operative position, faces toward the bone, the opening being open at the distal end of the bone plate and including a distal portion and a proximal portion, the distal portion having a width that is smaller than a width of the proximal portion, the width being a dimension between two longitudinal sides of the opening extending parallel to a longitudinal axis of the bone plate, the bone plate further including at least one bone fixation element receiving opening extending therethrough from the first surface to the second surface, an insert including a head portion and a base portion, the base portion being sized and shaped to be slidably mounted within the proximal portion of the opening, a diameter of the base portion being larger than a width of the distal portion of the opening such that the base portion, when positioned within the proximal portion of the opening, is prevented from exiting the opening through the distal portion thereof, the insert further including a central fixation element receiving hole configured to receive a bone fixation element therethrough and a bone fixation element configured to be inserted through the central fixation element receiving hole and into the intramedullary nail through hole to couple the bone plate to the intramedullary nail.

BRIEF DESCRIPTION

DETAILED DESCRIPTION

Figure 1:
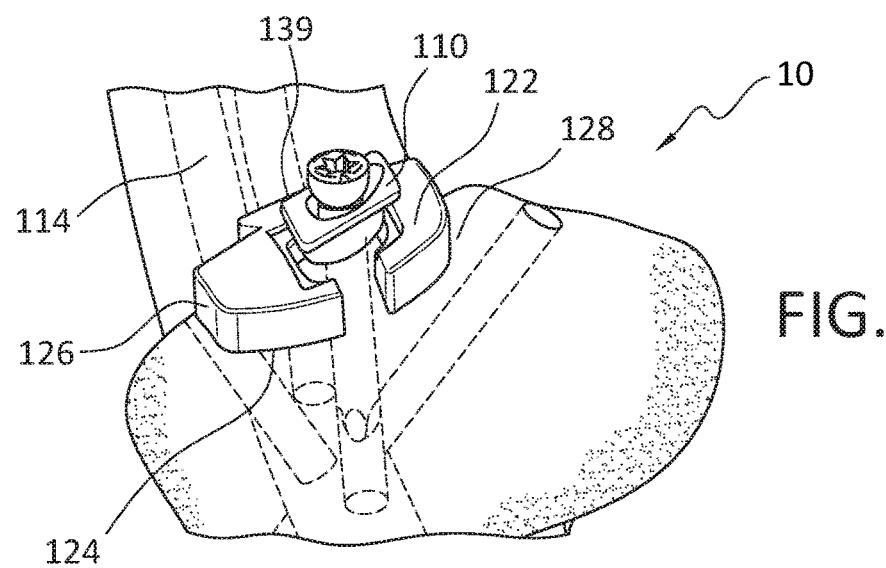
FIG. 1 shows a perspective view of a bone plate system according to an exemplary embodiment of the present disclosure.

The present disclosure may be further understood with reference to the following description and the appended drawings, wherein like elements are referred to with the same reference numerals. The present embodiments relate to the treatment of a bone and, in particular, relates the treatment of distal third femoral fractures and periprosthetic fractures. Exemplary embodiments describe a bone plate system including a bone plate configured to be positioned over a bone fracture and to be connected to an intramedullary nail inserted within the bone via a locking screw. The bone plate system includes a locking insert slidably insertable through a small gap in the bone plate to allow the surgeon to align and insert the locking screw into the intramedullary nail without interference with the bone plate. The slidable connection between the bone plate and the insert allows the surgeon to adjust the position of the bone plate relative to the bone and the intramedullary nail without removing the locking screw from the bone or the intramedullary nail. It should be noted that the terms "proximal" and "distal," as used herein, are intended to refer to a direction toward (proximal) and away from (distal) a user of the device.

Figure 2:
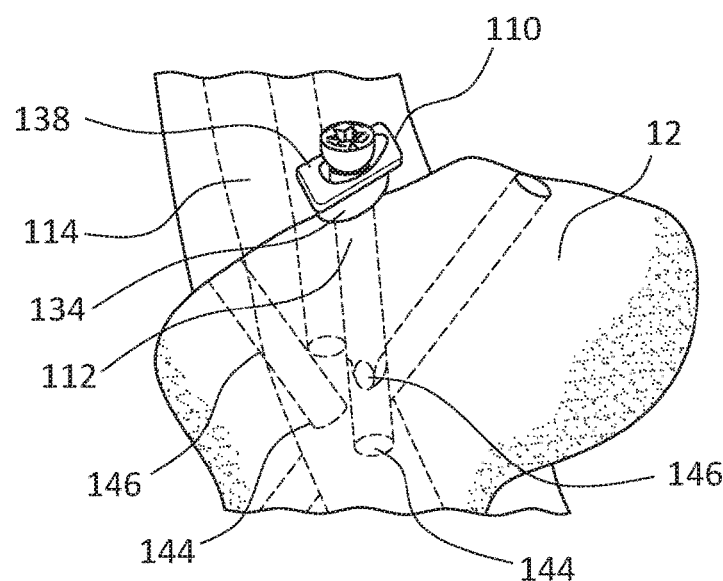
FIG. 2 shows a perspective view of an insert and a bone fixation element of the bone plate system of FIG. 1.
Figure 3:
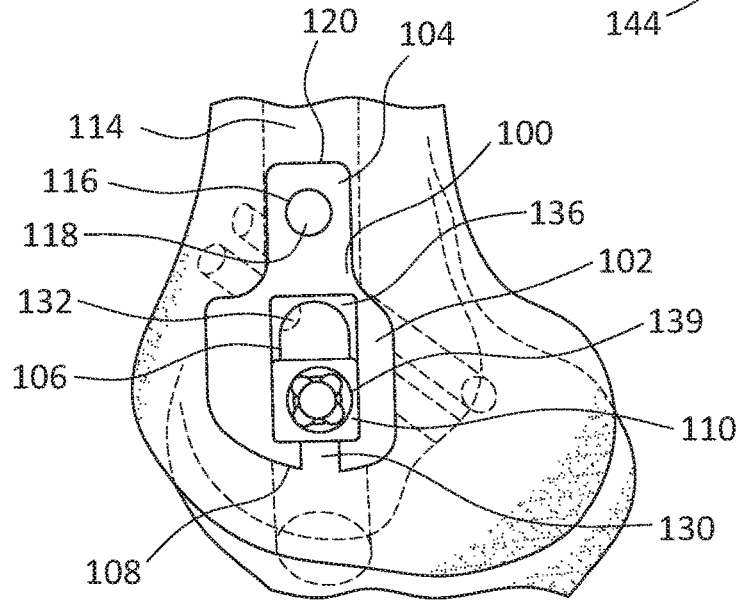
FIG. 3 shows a top plan view of a bone plate system according to an exemplary embodiment of the present disclosure.

FIGS. 1-6 show a system 10 according to an exemplary embodiment of the present disclosure for treating distal third fractures and periprosthetic fractures such as, for example, Vancouver Type A fractures (i.e., fractures in the greater trochanter) and/or Vancouver Type B fractures (i.e., in the proximity of the stem of a previously placed THA prosthetic or other intramedullary device). The system, according to a first embodiment, comprises a bone plate 100, as shown in FIGS. 1-3, configured to be implanted along a distal (or proximal) portion of the femur. The bone plate 100 includes a head portion 102 configured (i.e., sized and shaped) to fit in a desired position on, for example, the lateral femoral distal condyle of a femur 12 with a shaft portion 104 extending proximally therefrom. The head portion 102 of this embodiment includes a opening 106 open to a distal end of the bone plate 108 for receiving an insert 110 positioned about a locking screw 112 so that the head portion 102 may be fixed to the distal condyle and to an intramedullary nail 114 positioned within the medullary canal of the femur. The shaft portion 104 includes at least one bone fixation opening 116 for insertion of a bone fixation element 118 to provide plate location stability and/or interconnectivity to the distal proximal hole of the intramedullary nail.

As shown in FIGS. 2-3, and as described above, the bone plate 100 includes a head portion 102 configured to be positioned over the lateral condyle and a shaft portion 104 extending proximally therefrom to be positioned along a proximal portion of the lateral condyle or a distal portion of the femur shaft. The bone plate 100 extends along a longitudinal axis from a proximal end 120 to the distal end 108 and is defined via a first surface 122 which, when the bone plate 100 is in an operative position along a bone, faces away from the bone, and a second surface 124 which, when the bone plate 100 is in the operative position, faces the bone. Longitudinal sides 126, 128 extend longitudinally between the first and second surfaces 122, 124 from the proximal end 120 to the distal end 108. The second surface 124, in an exemplary embodiment, is contoured to an external surface of the portion of bone on which it is positioned. For example, in this embodiment, the second surface 124 is contoured to generally match the shape of the portion of the distal lateral condyle on which it is to be mounted. The head portion 102, in this embodiment, has a width (i.e., a distance between the longitudinal sides 126, 128) larger than a width of the shaft portion 104. However, it will be understood that the head and shaft portions 102, 104 may have any dimension depending on the procedure to be performed or the bone surface on which the bone plate 100 is to be implanted. Furthermore, one skilled in the art will understand that the bone plate 100 may include only a head portion 102 with no shaft portion.

Figure 4:
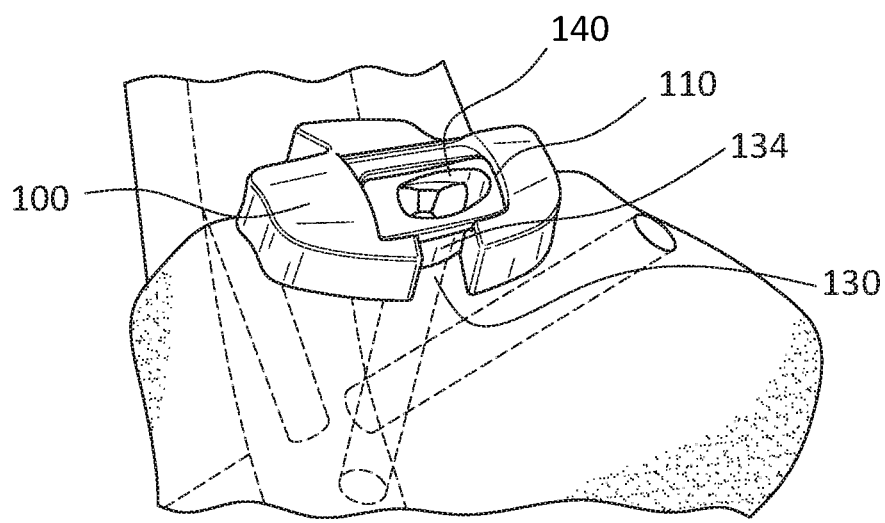
FIG. 4 shows another perspective view of the bone plate and insert of the bone plate system of FIG. 1.
Figure 5:
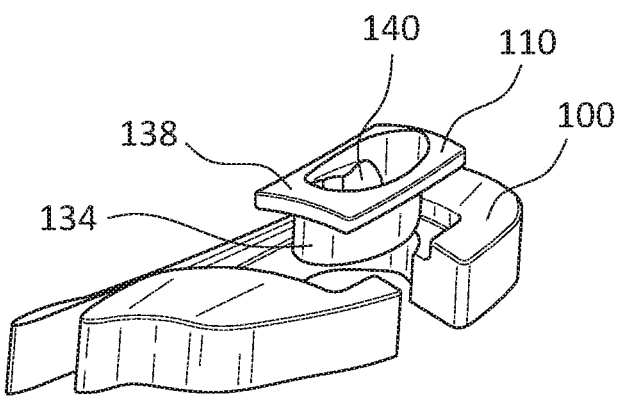
FIG. 5 shows a perspective view of the bone plate and insert of the bone plate system of FIG. 1.

The opening 106 extends from the first surface 122 to the second surface 124 and from a proximal end of the opening 106 to a distal end of the opening 106, and is open at the distal end 108 of the bone plate 100. A distal portion 130 of the opening 106 has a width (i.e., a distance between two longitudinal sides of the opening perpendicular to a longitudinal axis of the bone plate 100) that is smaller than a width at a proximal portion 132 of the opening. Specifically, the width of the distal portion 130 is sized and shaped to allow a shaft of the locking screw 112 to be slid therethrough and into the proximal portion 132 while preventing a base 134 of the insert 110 from sliding out of the opening 106 when seated in the proximal portion 132. Thus, the distal portion 130 may have a width equal to or slightly larger than a diameter of the locking screw shaft. However, the width of the distal portion 130 is smaller than a diameter of the base 134 of the insert 110 such that when the insert 110 is positioned within the proximal portion 132 of the plate opening 106, the insert 106 is locked therein, as will be described in further detail below. The first surface 122 of the plate may further include an indented portion 136 open to the opening 106 and sized to accommodate a head 138 of the insert 110. Specifically, in this embodiment, the indented portion extends around a perimeter of the opening 106. The indented portion 136 allows an outer surface 139 (opposing a bone facing surface 141) of the head 138 to sit flush with the first surface 122 when the locking screw 112 is fully inserted into the bone, as can be seen in FIG. 4. It will be understood by those skilled in the art that while the bone plate 100 of the present embodiment includes an indented portion 136 configured to accommodate a head 138 of the insert 110, in other embodiments, the bone plate 100 may not include an indented portion such that the head 138 sits on top of the bone plate first surface 122.

Figure 6:
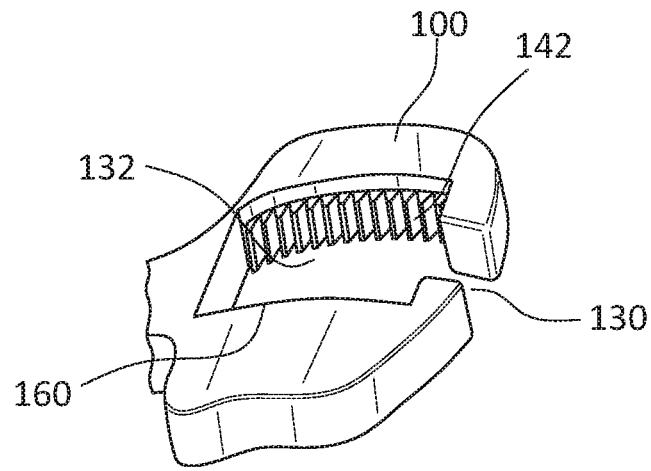
FIG. 6 shows a perspective view of the bone plate of the bone plate system of FIG. 1 according to another exemplary embodiment of the present disclosure.
Figure 7:
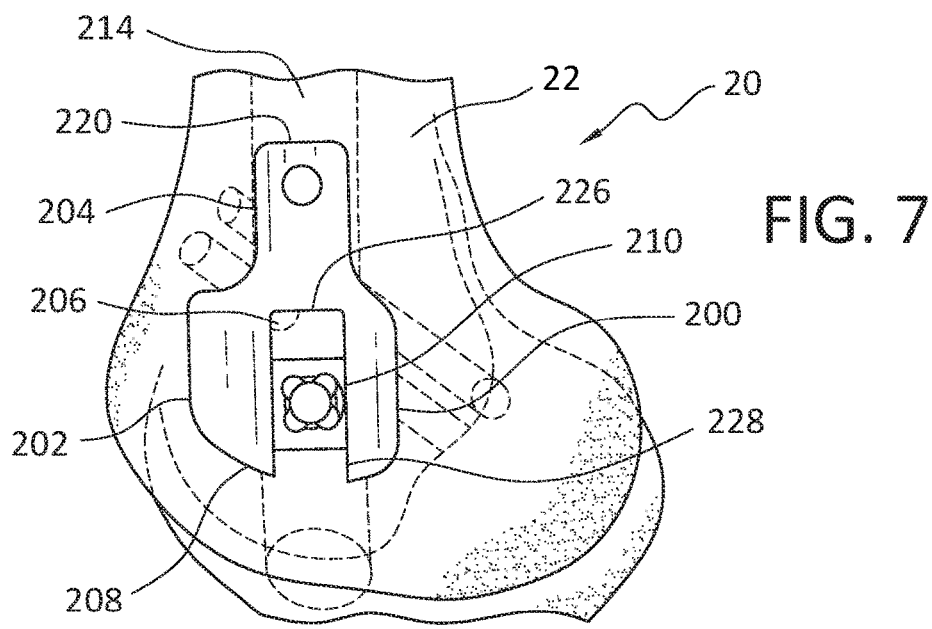
FIG. 7 shows a top plan view of a bone plate system according to a second exemplary embodiment of the present disclosure.
Figure 8:
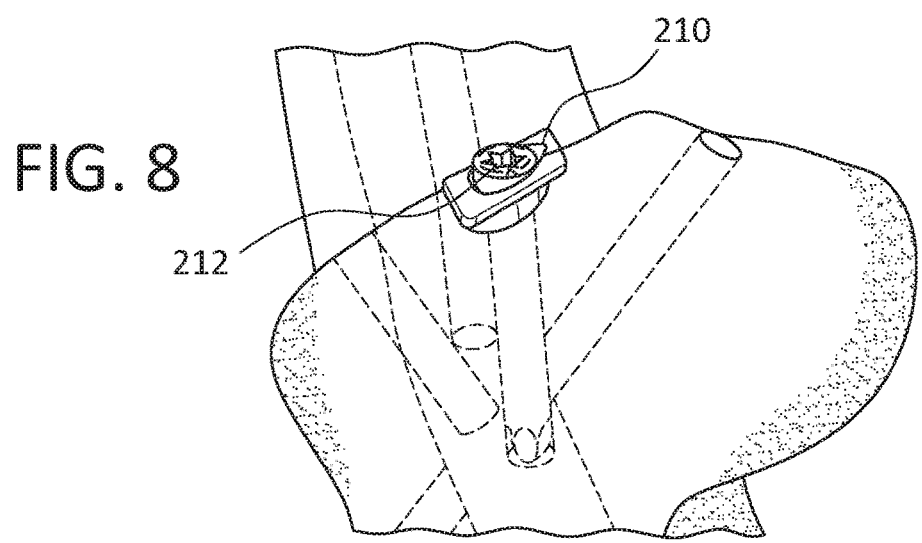
FIG. 8 shows a perspective view of an insert and a bone fixation element of the bone plate system of FIG. 7.

The indented portion 136 and opening 106 are sized and shaped to correspond with the outer profile of the insert 110. For example, as seen in FIG. 3, the indented portion 136 may have a substantially rectangular shape such that a rectangular (or square) head 138 of the insert 110 may be easily slid therealong when seated therein. Similarly, the proximal portion 132 of the opening 106, as shown in FIG. 3, may be substantially ovoid in shape such that the circular base 134 of the insert 110 may be slid therein to adjust a position of the bone plate 100. In an exemplary embodiment, an inner surface of the proximal portion 132 of the opening 106 may be smooth to allow the insert 110 to easily slide therethrough, allowing for repositioning of the bone plate 100 about the insert 110 and locking screw 112 when the locking screw 112 if fully inserted into the bone. However, as can be seen in FIG. 6, in another exemplary embodiment, the inner surface of the proximal portion 132 may include slots or knurls 142 configured to mate with corresponding slots or knurls (not shown) on the outer surface of the insert base 134 to lock the insert 110 in a desired location relative to the bone plate 100. In this embodiment, the plate 100 is positioned as desired on the bone prior to full insertion of the locking screw 112 into the bone.

The shaft portion 104 of the bone plate 100, in this embodiment, includes a single opening 116 extending therethrough from the first surface 122 to the second surface 124. It will be understood by those of skill in the art, however, that a single opening 116 is exemplary only and that the shaft portion 104, or the head portion 102, may have any number of openings 116 extending therethrough in any of a variety of spacings and configurations. For example, in some embodiments, the openings 116 may be aligned along the longitudinal axis of the bone plate 100 or may be staggered relative to the longitudinal axis of the bone plate 100. In this exemplary embodiment, the opening 116 is intended to receive a screw or fixation element 118 to provide the bone plate 100 location stability and/or interconnectivity to holes 144 within the intramedullary nail 114. In another embodiment, the opening 116 is a variable angle locking hole through which a bone fixation element 118 such as, for example, a variable angle locking screw, may be inserted at any user selected angle (within a supported range of angulation) relative to central axes thereof as would be understood by those skilled in the art. Thus, the angle of the locking screw 118 can be chosen by the physician depending on the patient's anatomy and the location of the bone plate 100 relative to the fracture. The variable angle locking hole 116 is configured such that the bone fixation element 118, when inserted therethrough, works with the locking screw 112 inserted through the slotted opening 106 to provide compression to the bone about the fracture.

The insert 110, as discussed above, includes a base 134 and a head 138 and is sized and shaped to be positioned within the proximal portion 132 of the opening 106 and indented portion 136 of the bone plate 100. The base 134, in this embodiment, is substantially circular while the head 138 is substantially square-shaped. However, it will be understood by those skilled in the art that the base 134 and head 138 may take any shape so long as outer profiles thereof are configured to mate with inner profiles of the opening 106 and indented portion 136, respectively, of the bone plate 100. As noted above, the base 134 of the insert 110 may, in an embodiment, have a substantially smooth outer surface configured to slide within a substantially smooth inner surface of the opening 106. However, in another embodiment, as described above, the insert 110 may include knurls or slots (not shown) configured to fit within mating knurls or slots 142 on the inner surface of the proximal portion of the opening 106. These mating components lock the insert 110 and the bone plate 100 relative to one another and the bone. The insert 110 includes a central fixation element receiving hole 140 configured to receive the locking screw 112 therethrough. The fixation element receiving hole 140 may be any type of hole including, for example, a variable angle hole through which the locking screw 112 may be inserted at an angle relative to a central axis thereof.

The locking screw 112 may be any type of bone screw configured to be inserted through a bone and into a through hole of the intramedullary nail 114 to fix the bone plate 100 to the bone. In an exemplary embodiment, the locking screw 112 is a variable angle locking screw that is capable of being inserted through the insert 110 at an angle relative to the central axis of the insert 100. The locking screw 112 may be a self-tapping screw or may require a bore to be drilled through the bone prior to insertion therein.

As indicated previously, the bone plate 100 is used in conjunction with an intramedullary nail 114, as shown in FIGS. 1-4. Referring to FIG. 1, the intramedullary nail 114 is shown positioned in the medullary canal of a femur. The nail 114 may be of any suitable design and is provided with one or more through holes 144 to accommodate one or more screws or bone fixation elements 118 inserted through the openings 116 in the bone plate 100. As noted above, these openings 116 are intended to provide the bone plate 100 with location stability and/or interconnectivity to the through holes 144 of the intramedullary nail 114. Additional screw holes 144 may be provided to permit transverse retaining screws or bolts 146 to be inserted at the distal end of the nail. In an exemplary embodiment, the screw holes 146 extend at different, divergent angles than each other and the orientation of the bone fixation element receiving hole 140, which is generally orthogonal with respect to the bone plate 100. These different angles improve fixation by allowing angled insertion of the transverse retaining screws 146 into different portions of the fragmented bone.

Figure 9:
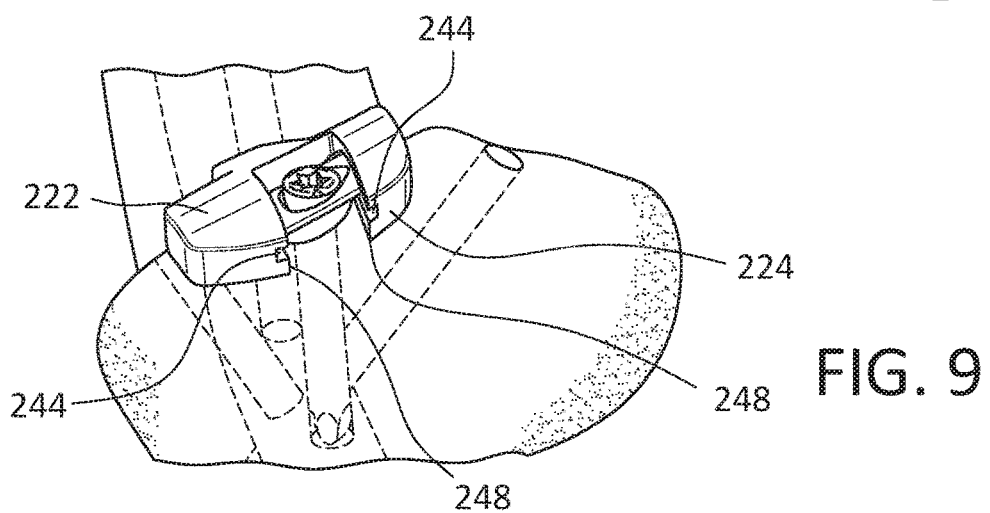
FIG. 9 shows another perspective view of the bone plate and insert of the bone plate system of FIG. 7.
Figure 10:
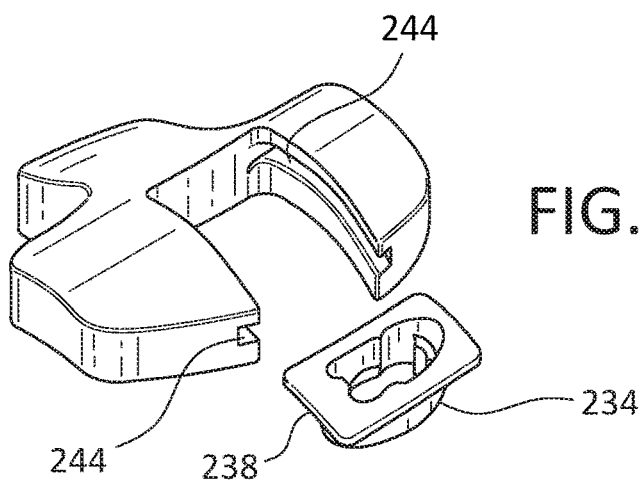
FIG. 10 shows a perspective view of the bone plate and insert of the bone plate system of FIG. 7.

As shown in FIGS. 7-10, a bone plate system 20 including a bone plate 200 configured to be attached to a bone 22, an insert 210, a locking screw 212, and an intramedullary nail 214 is substantially similar bone plate system 10 except as described herein. Specifically, the insert 210, in this embodiment, is configured to be slidably received within sliding ledges 244 of an opening 206 in the bone plate 200, as can be seen in FIG. 9.

The bone plate 200, as with bone plate 100, includes a head portion 202 and a shaft portion 204 extending proximally therefrom configured to be positioned over the distal lateral condyle of a femur bone 22. The bone plate 200 extends along a longitudinal axis from a proximal end 220 to a distal end 208 and is defined via a first surface 222 which, when the bone plate 200 is in an operative position along a bone, faces away from the bone, and a second surface 224 which, when the bone plate 200 is in the operative position, faces the bone. The opening 206 extends from the first surface 222 to the second surface 224 and from a proximal end 226 to a distal end 228 open at the distal end 208 of the bone plate 200. However, unlike the opening 106, the width of the opening 206 (i.e., a distance between the longitudinal sides of the opening in a direction perpendicular to a longitudinal axis of the bone plate 200) is uniform from the proximal end 226 to the distal end 228. The sliding ledges 244 are formed within the inner longitudinal surfaces 248 of the opening 206. The sliding ledges 244 extend from the proximal end 226 to the distal end 228 of the opening 206 and are open at the distal end 228. The ledges 244 are sized and shaped to receive a head 238 of the insert 210 such that the insert 210 is easily slidable therein so that the bone plate 200 may be positioned as desired relative to the insert 210 and locking screw 212. Thus, to allow the bone plate 200 to sit flush against the bone when the insert 210 is positioned within the sliding ledges 244, a depth of the base 234 of the insert 210 (i.e., a dimension between a bone-facing surface of the base 234 and the bone-facing surface of the head 238) is approximately the same or smaller than a depth of the bone plate 200 between the second surface 224 and the ledges 244.

Figure 11:
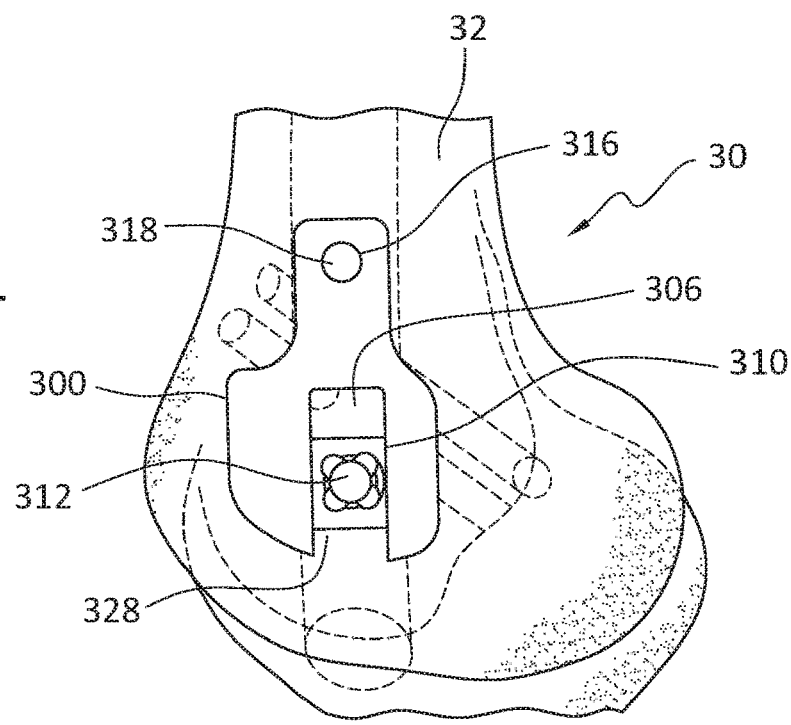
FIG. 11 shows a top plan view of a bone plate system according to a third exemplary embodiment of the present disclosure.
Figure 12:
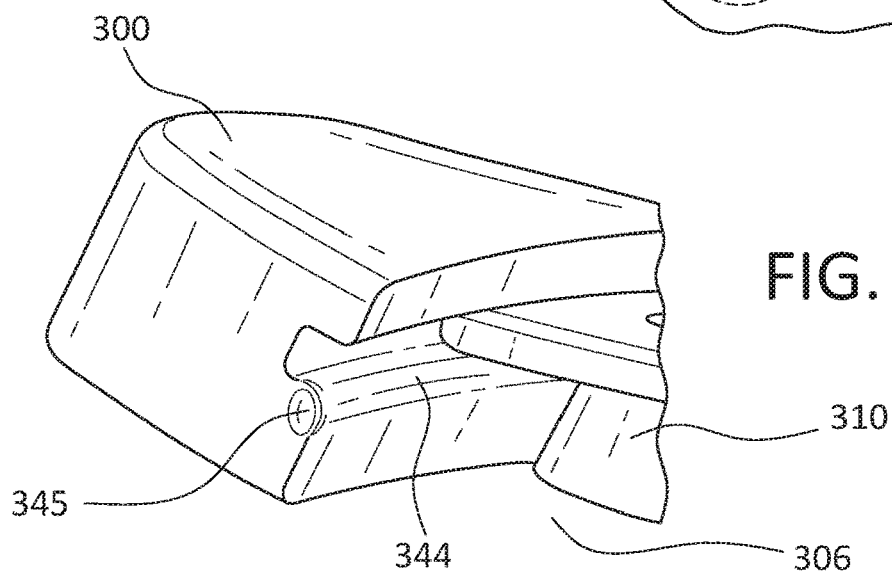
FIG. 12 shows a perspective view of a distal end of the bone plate system of FIG. 11.

In another exemplary embodiment shown in FIGS. 11-12, a bone plate system 30 is substantially the same as the bone plate system 20 except that the sliding ledges 344 may be peened or closed at the distal end 328 of the opening 306 to prevent the insert 310 from sliding out of the sliding ledges 344, as shown in FIG. 12. In this embodiment, the insert 310 is assembled with the bone plate 300 and the ends 345 of the ledges 344 peened during manufacturing of the bone plate system 30. Thus, in use, a locking screw 312 is used to align the bone plate 300 with the intramedullary nail 314 such that the bone plate 300, with the insert 310, is slid along the locking screw 312 and onto the bone surface.

According to an exemplary surgical method using the above-describe system, the intramedullary nail 114 having the structure shown in FIGS. 1-4 is inserted into the shaft of a femur 12, in any conventional manner. The locking screw 112, with the insert 110 incorporated thereon, is then partially inserted into a bone in alignment with a desired through hole 142 of the intramedullary nail 114 near the portion of the femur to be treated such as, for example, near a eriprosthetic fracture. That is, the locking screw 112 is inserted to a depth within the bone that provides a clearance between the bone and a bone-facing surface of the base of the insert 110 that is greater than a distance between the first and second surfaces of the bone plate 100, as shown in FIG. 1. The bone plate 100 may then be positioned over the target portion of the femur without any interference with the locking screw 112. Specifically, the locking screw 112 is slid through the distal portion of the opening 106 of the bone plate 100 until the bone plate is positioned as desired on the lateral femoral distal condyle of the femur 12, as shown in FIG. 2. Once the bone plate 100 has been positioned along the bone, in a desired position as described above, the locking screw 112 is tightened until the insert 110 is seated within the proximal portion 132 of the opening 106 in the desired location. Another bone fixation element 118 such as, for example, a screw, may be inserted through the opening 116 to fix the bone plate 100 to the bone and provide plate location stability and/or interconnectivity to the distal hole of the intramedullary nail, as shown in FIG. 3.

In some circumstances, the physician may need to reposition the bone plate 100 over the desired portion of the bone. In these instances, the bone plate 100 may be repositioned about the insert 110, prior to insertion of the bone fixation element 118, by, for example, sliding the bone plate 100 about its longitudinal axis or rotating the bone plate 100 about the insert 110 until the bone plate 100 is placed as desired. After the bone plate 100 has been repositioned along the bone as desired, the bone fixation element 118 is inserted through the opening 116 to, in an exemplary embodiment, provide stability to the bone plate 100 relative to the intramedullary nail 114. In another embodiment, the bone fixation element 118 may be inserted at an angle that, in combination with the locking screw 112, applies compression to the fracture, as described above.

Similarly, bone plate 200 is positioned over the bone relative to the fracture to the treated in the same manner described above with respect to bone plate 100 except that the head 238 of the insert 210 is inserted into the sliding ledges 244 of the bone plate 100 when positioning the bone plate as desired, as described above.

It will be understood by those of skill in the art that modifications and variations may be made in the structure and methodology of the present invention, without departing from the spirit or scope of the invention. Thus, it is intended that the present invention cover the modifications and variations of this invention, provided that they come within the scope of the appended claims and their equivalents.

What is claimed is:

1. A bone plate for treating periprosthetic fractures comprising:
    a body extending from a proximal end to a distal end and including an elongated opening extending therethrough from a first surface of the body which, when the bone plate is in an operative position, faces away from a bone, to a second surface which, when the bone plate is in the operative position, faces toward the bone,
    the elongated opening being open at the distal end of the body and including a distal portion and a proximal portion, the distal portion having a width that is smaller than a width of the proximal portion, the width being a dimension between two longitudinal sides of the elongated opening extending parallel to a longitudinal axis of the body, the body further including at least one bone fixation element receiving aperture extending therethrough from the first surface to the second surface;
    wherein the proximal portion of the elongated opening has an outer portion with a first width at the first surface of the body and an inner portion with a second width at the second surface of the body, the second width being smaller than the first width; and
    an insert including a head portion and a base portion, the base portion being sized and shaped to be mounted within the proximal portion of the elongated opening, a diameter of the base portion being larger than the width of the distal portion of the elongated opening such that the base portion, when positioned within the proximal portion of the elongated opening, is prevented from exiting the elongated opening through the distal portion thereof, the insert further including a central fixation element receiving hole configured to receive a bone fixation element therethrough;
    wherein the head portion is configured to fit within the outer portion of the proximal portion of the elongated opening;
    wherein the base portion is configured to longitudinally translate within the proximal portion of the elongated opening.

2. The bone plate of claim 1, wherein the bone plate includes a head portion and a shaft portion, the elongated opening being positioned in the head portion of the bone plate, the shaft portion extending proximally from the head portion of the bone plate and including at least one bone fixation receiving element aperture.

3. The bone plate of claim 2, wherein the first surface of the body further includes an indented portion in communication with the proximal portion of the elongated opening, the indented portion extending about the proximal portion of the elongated opening and having a perimeter that is larger than a perimeter of the proximal portion, the indented portion being sized and shaped to receive the head portion of the insert.

4. The bone plate of claim 3, wherein the indented portion has a depth sized to accommodate a depth of the head portion of the insert, the depth being a dimension extending perpendicular to the longitudinal axis of the body.

5. The bone plate of claim 1, wherein the second surface of the bone plate is contoured to a shape of a distal lateral condyle.

6. The bone plate of claim 1, wherein the central fixation element hole is a variable angle locking hole.

7. The bone plate of claim 1, wherein an inner surface of the proximal portion of the elongated opening includes a plurality of slots configured to mate with a plurality of slots on the insert base received therein to lock the insert in position relative to the bone plate.

8. A system for treating periprosthetic fractures comprising:
    an intramedullary nail including a through hole configured to receive a bone fixation element;
    a bone plate extending from a proximal end to a distal end and including an elongated opening extending therethrough from a first surface of the bone plate which, when the bone plate is in an operative position, faces away from a bone, to a second surface which, when the bone plate is in the operative position, faces toward the bone, the elongated opening being open at the distal end of the bone plate and including a distal portion and a proximal portion, the distal portion having a width that is smaller than a width of the proximal portion, the width being a dimension between two longitudinal sides of the elongated opening extending parallel to a longitudinal axis of the bone plate, the bone plate further including at least one bone fixation element receiving aperture extending therethrough from the first surface to the second surface;

wherein the proximal portion of the elongated opening has an outer portion with a first width at the first surface of the body and an inner portion with a second width at the second surface of the body, the second width being smaller than the first width; and an insert including a head portion and a base portion, the base portion being sized and shaped to be mounted within the proximal portion of the elongated opening, a diameter of the base portion being larger than the width of the distal portion of the elongated opening such that the base portion, when positioned within the proximal portion of the elongated opening, is prevented from exiting the elongated opening through the distal portion thereof, the insert further including a central fixation element receiving hole configured to receive a bone fixation element therethrough, wherein the base portion is configured to longitudinally translate within the proximal portion of the elongated opening; and wherein the head portion is configured to fit within the outer portion of the proximal portion of the elongated opening;

a bone fixation element configured to be inserted through the central fixation element receiving hole and into the intramedullary nail through hole to couple the bone plate to the intramedullary nail.

9. The system of claim 8, wherein the bone plate includes a head portion and a shaft portion, the elongated opening being positioned in the head portion of the bone plate, the shaft portion extending proximally from the head portion of the bone plate and including at least one bone fixation element receiving aperture.

10. The system of claim 9, wherein the first surface of the bone plate further includes an indented portion in communication with the proximal portion of the elongated opening, the indented portion extending about the proximal portion of the elongated opening and having a perimeter that is larger than a perimeter of the proximal portion, the indented portion sized and shaped to receive the head portion of the insert.

11. The system of claim 8, wherein the second surface of the bone plate is contoured to the shape of a distal lateral condyle.

12. The system of claim 8, wherein the central fixation element hole is a variable angle locking hole.

13. The system of claim 8, wherein an inner surface of the proximal portion of the elongated opening and an outer surface of the insert base each includes a plurality of slots configured to mate with one another to lock the insert in position relative to the bone plate.

14. The system of claim 8, wherein the bone fixation element is a variable angle locking screw.

15. A bone plate for treating periprosthetic fractures comprising:

a body with a longitudinal axis, the body extending from a proximal end to a distal end and including:

at least one bone fixation element receiving aperture extending therethrough from a first surface configured to face away from a bone to a second surface configured to face toward the bone, and an elongated opening extending from the first surface to the second surface, wherein:

the elongated opening is parallel to the longitudinal axis of the body, and the elongated opening includes a distal portion having an opening at the distal end of the body, and a proximal portion, wherein the distal portion of the elongated opening has a width that is smaller than a width of the proximal portion of the elongated opening;

wherein the proximal portion of the elongated opening has an outer portion having a first width at the first surface and an inner portion with a second width at the second surface, the first width being larger than the second width; and an insert including a head portion configured to be received within the outer portion of the elongated opening and a base portion configured to be received within the inner portion of the elongated opening, the base portion being slidably mounted within the proximal portion of the elongated opening, a diameter of the base portion being larger than the width of the distal portion of the elongated opening such that the base portion is prevented from exiting the elongated opening through the distal portion thereof, the insert further including a central fixation element receiving hole configured to receive a bone fixation element therethrough;

wherein the base portion linearly translates in a direction which is parallel to the longitudinal axis of the body.

* * * * *